(12) United States Patent
Nguyen

(10) Patent No.: US 7,385,692 B1
(45) Date of Patent: Jun. 10, 2008

(54) METHOD AND SYSTEM FOR FIBER OPTIC DETERMINATION OF GAS CONCENTRATIONS IN LIQUID RECEPTACLES

(75) Inventor: Quang-Viet Nguyen, Richmond Heights, OH (US)

(73) Assignee: The United of America as represented by the Administrator of NASA, Washington, DC (US)

(*) Notice: Subject to any disclaimer, the term of this patent is extended or adjusted under 35 U.S.C. 154(b) by 60 days.

(21) Appl. No.: 11/412,924

(22) Filed: Apr. 28, 2006

(51) Int. Cl.
*G01J 3/44* (2006.01)
*G01N 21/65* (2006.01)

(52) U.S. Cl. ..................................................... 356/301
(58) Field of Classification Search ................ 356/301, 356/341.3; 359/341.3
See application file for complete search history.

(56) References Cited

U.S. PATENT DOCUMENTS

| | | | |
|---|---|---|---|
| 5,450,883 A | 9/1995 | Payne et al. | 141/59 |
| 5,542,458 A | 8/1996 | Payne et al. | 141/7 |
| 5,988,232 A | 11/1999 | Koch et al. | 141/59 |
| 6,028,666 A * | 2/2000 | Boss et al. | 356/301 |
| 6,082,415 A | 7/2000 | Rowland et al. | 141/59 |
| 6,100,975 A * | 8/2000 | Smith et al. | 356/301 |
| 6,167,747 B1 | 1/2001 | Koch et al. | 73/19.03 |
| 6,216,540 B1 * | 4/2001 | Nelson et al. | 73/633 |
| 6,283,173 B1 | 9/2001 | Osborne | 141/83 |
| 6,325,112 B1 | 12/2001 | Nanaji | 141/4 |
| 6,499,516 B2 | 12/2002 | Pope et al. | 141/59 |
| 6,614,523 B1 | 9/2003 | Boss et al. | 356/301 |
| 6,622,757 B2 | 9/2003 | Hart et al. | 141/7 |
| 6,634,598 B2 * | 10/2003 | Susko | 244/135 R |
| 6,712,101 B1 | 3/2004 | Nanaji | 141/83 |
| 6,739,399 B2 | 5/2004 | Wagner et al. | 169/45 |
| 2003/0035205 A1 | 2/2003 | Zisk, Jr. | 359/341.3 |

\* cited by examiner

*Primary Examiner*—F. L. Evans
*Assistant Examiner*—Abdullahi Nur
(74) *Attorney, Agent, or Firm*—Squire, Sanders & Dempsey, L.L.P.

(57) ABSTRACT

A system for determining gas compositions includes a probe, inserted into a source of gaseous material, the probe having a gas permeable sensor tip and being capable of sending and receiving light to and from the gaseous material, a sensor body, connected to the probe, situated outside of the source and a fiber bundle, connected to the sensor body and communicating light to and from the probe. The system also includes a laser source, connected to one portion of the fiber bundle and providing laser light to the fiber bundle and the probe a Raman spectrograph, connected to another portion of the fiber bundle, receiving light from the probe and filtering the received light into specific channels and a data processing unit, receiving and analyzing the received light in the specific channels and outputting concentration of specific gas species in the gaseous material based on the analyzed received light.

26 Claims, 14 Drawing Sheets

METHOD AND SYSTEM FOR FIBER OPTIC DETERMINATION OF GAS CONCENTRATIONS IN LIQUID RECEPTACLES

ORIGIN OF THE INVENTION

The invention described herein was made by employees of the United States Government and may be manufactured and used by or for the Government for Government purposes without payment of any royalties thereon or therefore.

BACKGROUND OF THE INVENTION

1. Field of Invention

The present invention relates to systems for determining the chemical composition of gaseous mixtures. In particular, the present invention is directed to systems and processes for determining the presence and composition of oxygen, nitrogen and hydrocarbons, among other gaseous constituents, in gaseous mixtures. In specific embodiments, the invention allows for the use of optical spectroscopy to analyze the gaseous compositions without exposing the interiors of liquid receptacles to the outside or sources of ignition.

2. Description of Related Art

There are many environments where it is important to measure with great accuracy the composition of gaseous materials in real-time. These measurement environments can include measuring to determine the presence of harmful gases, the determination of intrinsic properties, or the monitoring of percentages of specific compositions. Such environments include a natural gas pipeline where monitoring of species can determine heating values or in monitoring of respiration or anesthesiological values in the delivery of medical treatments. The ability to measure such quantities in real-time would be of great interest to many fields of endeavor.

One such issue of determination of compositions of gaseous materials occurs with fuel tanks. In the area of aircraft safety, there exists a need to reduce or eliminate the explosion hazard posed by the mixture of fuel vapors and oxygen contained in the space above the liquid (ullage) of a fuel tank. In a conventional aircraft fuel tank, the ullage will contain a mixture of jet fuel vapor and air. As the fuel is used up, more air from the outside is drawn in to fill the ullage created by the spent liquid fuel. In order for a fire or explosion hazard to exist, there needs to be three things: fuel, oxygen, and energy to ignite the mixture.

Since the fuel cannot be removed, and ignition sources (such as static electricity, lightning, or even a terrorist strike) may exist, the oxygen needs to be reduced or removed. The oxygen is removed by displacing it with nitrogen enriched air that is produced from an on-board inert gas generation system (OBIGGS) that feeds nitrogen-enriched air into the fuel tank to eventually displace the oxygen. Such systems are expensive to operate continuously (from a fuel economy standpoint), and it also desirable to know when the fuel tank has been rendered inert to a safe level (typically less than 9% by volume). Thus, a way to measure the relative or absolute oxygen and/or nitrogen concentrations in the ullage of fuel tank is needed.

Unique features of such a problem include that the sensor system cannot introduce any intrinsic fire or explosion hazard such as would be the case with electronic wire-based sensors and the sensor system needs to provide a measurement of the oxygen concentration over a wide temperature (−40 C to 71 C) and pressure (0.2 atm to 1.0 atm) range corresponding to the conditions inside an airplane fuel tank over the flight envelope. The sensor needs to be reliable and robust and needs to be compact and lightweight in order to be fitted to an airplane's fuel system. The sensor should preferably also measure nitrogen and fuel vapor concentrations for a secondary check of the OBIGGS system performance and the system needs to work reliably and unattended with no maintenance for up to 1 year (time between fuel tank service checks). The system should also preferably be low-cost for deployment on the entire fleet of commercial aircraft. Specifically, the sensor needs to be able to measure the absolute concentration of $O_2$ at the following condition which represents the lowest absolute concentration of molecular oxygen in the flight envelope. The sensor needs to have a 1% measurement precision and accuracy in measuring 5% $O_2$ (by volume) at a temperature of −1 C and a pressure of 0.2 atm, with the balance gases being nitrogen and fuel vapor.

Prior art systems have relied on electrochemical oxygen sensors or paramagnetism oxygen sensors. A newer technique, that uses the effect of oxygen fluorescence quenching on a dye that is fiber optically illuminated by a blue LED, has been proposed. Other techniques have been proposed to use diode laser absorption spectroscopy near 760 nm to measure oxygen. However, the first two techniques above require exposing the ullage gases to a sensor that is connected to a wire which can potentially be a source of sparks or electrostatic ignition. Furthermore, the electrochemical sensor typically uses a heated element that reacts and consumes the oxygen that it is sensing, producing a fire hazard. The fiber optic fluorescence quenching sensors that utilize the intensity of an oxygen sensitive dye that is illuminated with a blue LED have also been proposed but this sensor is prone to large drifts when exposed to temperature changes. The drift of the fluorescence quenching type sensor is so great that it renders the technique ineffective for the reliable measurement of oxygen concentration in the ullage of a fuel tank. The diode laser absorption technique is problematic because it requires a diode laser to tune and lock onto specific oxygen absorption lines, the technique requires windows for optical access which can get dirty from fuel deposits. None of these techniques can measure both nitrogen and oxygen concentration to provide an accurate mixing ratio without having to assume that the balance is nitrogen. Also, none of these other techniques are able to provide fuel vapor concentration.

As such, there is a need for a system that does not introduce any intrinsic fire or explosion hazard, provides measurements of gaseous concentrations over wide temperature and pressure ranges and which is reliable and robust. There is also a need for a system that is compact and lightweight and be low-cost for deployment in many detection environments.

SUMMARY OF THE INVENTION

According to one embodiment of the invention, a system for determining gas compositions includes a probe, inserted into a source of gaseous material, the probe having a gas permeable sensor tip and being capable of sending and receiving light to and from the gaseous material, a sensor body, connected to the probe, situated outside of the source and a fiber bundle, connected to the sensor body and communicating light to and from the probe. The system also includes a laser source, connected to one portion of the fiber bundle and providing laser light to the fiber bundle and the probe a Raman spectrograph, connected to another portion of the fiber bundle, receiving light from the probe and filtering the received light into specific channels and a data processing unit, receiving and analyzing the received light in the specific channels and outputting concentration of specific gas species in the gaseous material based on the analyzed received light.

Additionally, the system may be used where the gaseous material source is a fuel tank and the system is configured to determine the concentration of the specific gas species in a ullage of the fuel tank. Also, the system may be used where the gaseous material source is a natural gas pipeline and the system is configured to determine the concentration of the specific gas species in the natural gas pipeline. Also, the system may be used where the gaseous material source is a gas sampling chamber receiving gases exhaled from a medical patient and the system is configured to determine the concentration of the specific gas species in the exhaled gases. Also, the system may be used where the gaseous material source is a gas sampling chamber receiving anesthesiological gases provided to a medical patient and the system is configured to determine the concentration of the specific gas species in the anesthesiological gases.

Additionally, the probe may receive optical fibers from the fiber bundle such that optical fibers for laser excitation of the gaseous material are surrounded by other optical fibers for Raman light collection. The Raman spectrograph may include discrete optical detectors, with each discrete optical detector detecting filtered light from one channel of the specific channels, or a prism-grating type spectrograph or dichroic mirrors and spectral band pass filters to filter the received light into the specific channels. The probe may further include a cleaning jet, receiving cleaning fluid and used to clean a light receiving surface of the probe and a drain and vent hole that allows for the cleaning fluid and other liquids to be wicked away. The gas permeable sensor tip further includes a series of baffles and labyrinth plates to limit impingement of liquids to a gas permeable membrane.

According to another embodiment, a method for determining gas compositions of a gaseous material includes the steps of receiving laser light, from a laser source, by a probe inserted into a source of gaseous material, the probe having a gas permeable sensor tip, receiving Raman light resulting from the laser light excitation of the gaseous material and communicating the Raman light to a Raman spectrograph via a fiber bundle. The method also includes filtering the received Raman light into specific channels, receiving and analyzing the light in the specific channels by a data processing unit and outputting concentrations of specific gas species in the gaseous material based on the analyzed received light.

According to another embodiment, a system for determining gas compositions of a gaseous material includes laser receiving means for receiving laser light, from a laser source, by a probe inserted into a source of gaseous material, the probe having a gas permeable sensor tip, Raman receiving means for receiving Raman light resulting from the laser light excitation of the gaseous material, communicating means for communicating the Raman light to a Raman spectrograph via a fiber bundle, spectrographic means for filtering the received Raman light into specific channels, analyzing means for receiving and analyzing the light in the specific channels by a data processing unit and outputting means for outputting concentrations of specific gas species in the gaseous material based on the analyzed received light.

These and other variations of the present invention will be described in or be apparent from the following description of the preferred embodiments.

BRIEF DESCRIPTION OF THE DRAWINGS

For the present invention to be easily understood and readily practiced, the present invention will now be described, for purposes of illustration and not limitation, in conjunction with the following figures.

DETAILED DESCRIPTION OF PREFERRED EMBODIMENTS

The present invention seeks to provide quantitative and accurate measurements of the compositions of gaseous materials in liquid receptacles. The present invention also seeks, in one embodiment, to provide a quantitative and accurate measurement of the concentration of nitrogen, oxygen, and fuel vapor in the ullage of a fuel tank. This information is needed in order to provide control information for an OBIGGS, and also for the determination of the appropriate levels of inerting required for safety. The ullage gas sensor system is based on spontaneous vibrational laser Raman scattering from the species of interest. Raman scattering is used because it is one of the few optical techniques that permits the simultaneous multi-species measurements of chemical concentrations.

The system provides an accurate and quantitative identification of the above gases with an accuracy of better than 1% (by volume) over approximately a 1 minute time duration. The technology described in this disclosure is a critically enabling sensor technology for the feedback control of on-board inert gas generation systems (OBIGGS) that are used to inert aircraft fuel tanks for the prevention of aircraft fuel tank explosions and fires. The system is simple, compact, lightweight, and can be made robust and reliable for aircraft use. Furthermore, this sensor technology does not present an intrinsic fire or explosion safety hazard compared to electrically-based sensors that require wiring.

Figure 1:
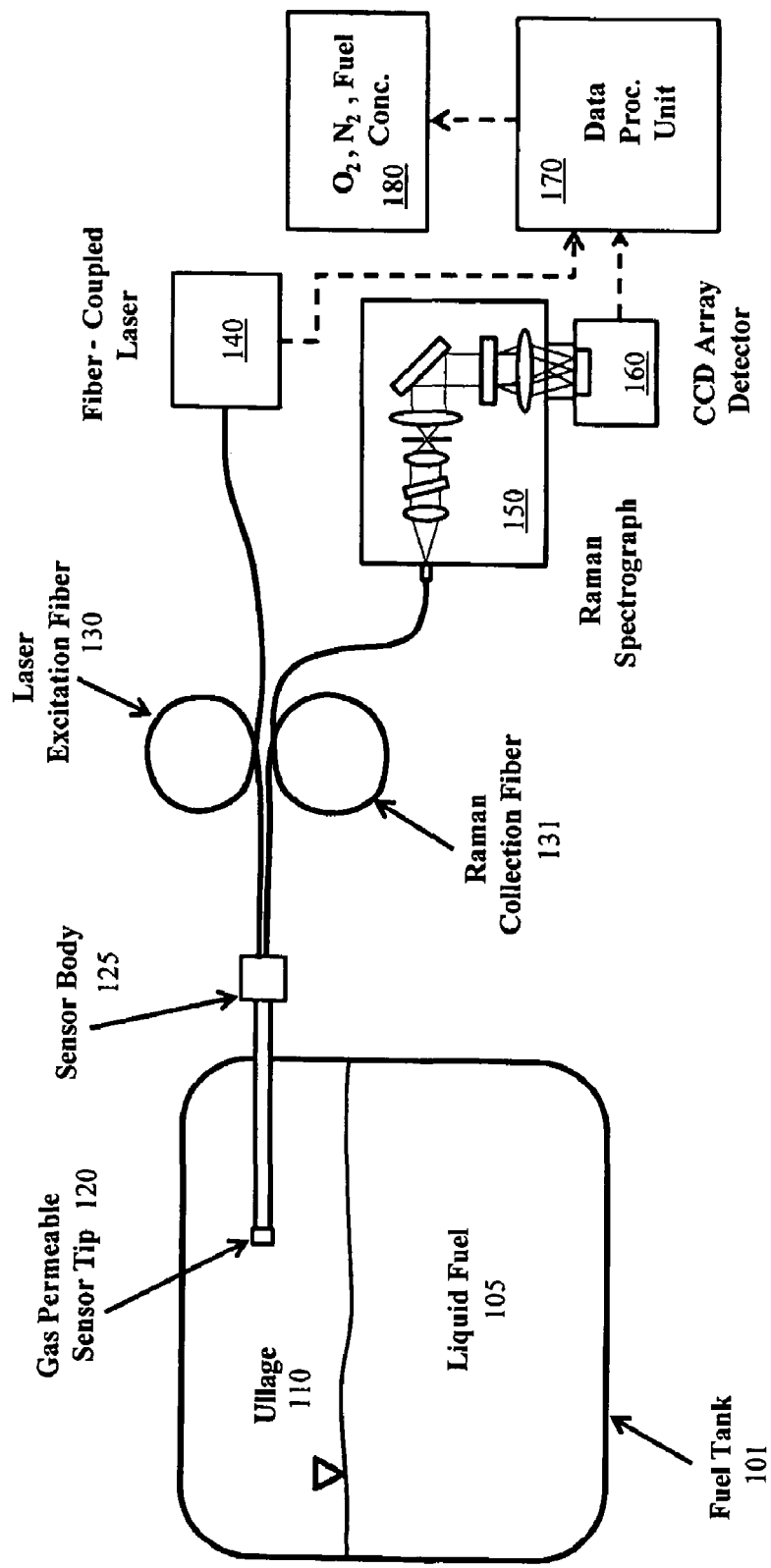
FIG. 1 illustrates a fiber optic ullage oxygen/nitrogen sensor system, according to one embodiment of the present invention.

The Raman scattering is implemented using fiber optic coupling which does not pose an intrinsic explosion or fire hazard. In addition, fiber optic coupled Raman scattering permits the sensor probe to be located remotely from the laser and spectrograph. FIG. 1 shows a schematic of the overall system which uses a compact continuous wave (CW) diode pumped solid state (DPSS), or similar laser with 532 nm emission. Although a pulsed laser (Q-switched) can be used to provide similar laser powers on average, pulsed lasers should not be used since they have high peak powers which pose an ignition problem. The sensor body 125 stays outside of the fuel tank 101, while the gas permeable sensor tip 120 is placed inside the ullage 110 of the tank, above the liquid fuel 105.

Schematic of fiber optic ullage oxygen/nitrogen sensor system provided in FIG. 1 has a fiber coupled laser 140, that may be a 20 mW 532 nm diode-pumped solid state (DPSS) frequency doubled Nd:YVO$_4$. It is noted that other types of lasers such as Nd:YAG can also be used. The laser is connected to the sensor body through a laser excitation fiber 130 and resultant light is collected into the Raman collection fiber 131. The Raman spectrograph 150 is a fast (f/1.8) axially transmissive type with holographic notch filter and holographic volume phase grating, in at least one embodiment. Conventional Czerny-Turner designs can be used but have lower optical throughput. The detector 160 is high-sensitivity thermo-electrically-cooled backside-illuminated CCD array, but discrete (or arrays of) PMT's or APD's can also be used. Laser power measurement data (from laser) is used to normalize Raman signal. It is noted that the laser and spectrograph/detector array can be remotely mounted away from the harsh environment of the fuel tank A data processing unit 170 is used to analyze the data and gas composition and concentration data is provided by unit 180.

Figure 2:
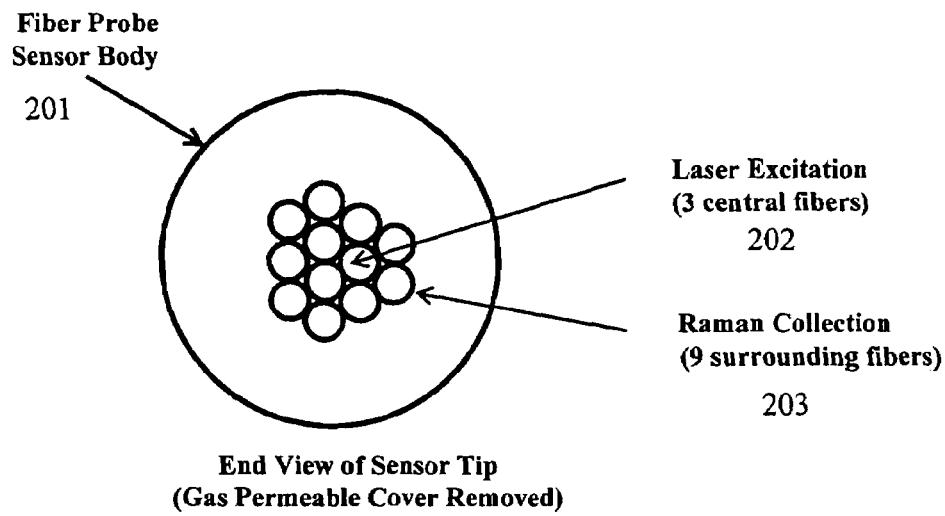
FIG. 2 provides a schematic of an end face of a fiber optic probe tip, according to one embodiment of the present invention.

The laser is lens-coupled into a multi-mode 200 μm dia core fiber for the fiber probe sensor body 201, which is the central fiber of a fiber bundle 202 arranged in a hexagonal-closest-packed geometry (shown in FIG. 2), that exposed to the ullage of a fuel tank. The Raman scattered light is collected by fibers 203 located around the central fiber (see FIG. 2) via proximity focusing. While FIG. 2 illustrates 3 laser excitation fibers and nine Raman collection fibers, that represents on a single embodiment. In one embodiment, all fibers used are 0.22 numerical aperture (NA), Cu-clad, 200 μm core dia silica, optimized for visible wavelength transmission. Overlap of volume between excitation fiber light cone and collection fiber cone is determined by numerical aperture (NA), diameter of fibers, and number of fibers. Fibers are assembled using metal soldering or brazing techniques with special metal-clad fibers (Cu or Au), in one embodiment. Metal clad fibers permit durable hermetic seals without fluorescence or fiber-crosstalk resulting from adhesive (epoxied) based designs.

The collection fibers are directed to a Raman spectrograph as shown in FIG. 1 which filters the Rayleigh (elastic) scattered light using a notch filter and disperses the Raman (in-elastic) scattered light into different wavelengths which are detected using a multi-channel light detector such as a CCD array. The signal from the detector is processed with an electronic circuit and/or a computer and software to provide a quantitative measure of the species concentration of $N_2$, $O_2$, and fuel vapor, in this embodiment. The vibrational Raman bands for $N_2$, $O_2$, and hydrocarbon fuel vapor (such as jet fuel) are centered at the following wavelengths: 607 nm, 580 nm, 630 nm, respectively for 532 nm wavelength excitation.

In order to collect the full vibrational band for each species, the spectral integration width for each vibrational band should be about 13 nm wide full-width-half-max (FWHM). These 13 nm wide spectral bands centered at the wavelength for each species can be referred to as a 'super-pixel'. In the case of a detector plane that is fitted with discrete fiber optic collection devices leading to discrete light detectors, or a detector plane fitted with discrete light detectors such as photomultiplier tubes (PMT) or avalanche photodiodes (APD), the same spectral width and center locations still have to be used in order to maximize the signal while minimizing the effects of spectral cross-talk or interference.

Figure 3:
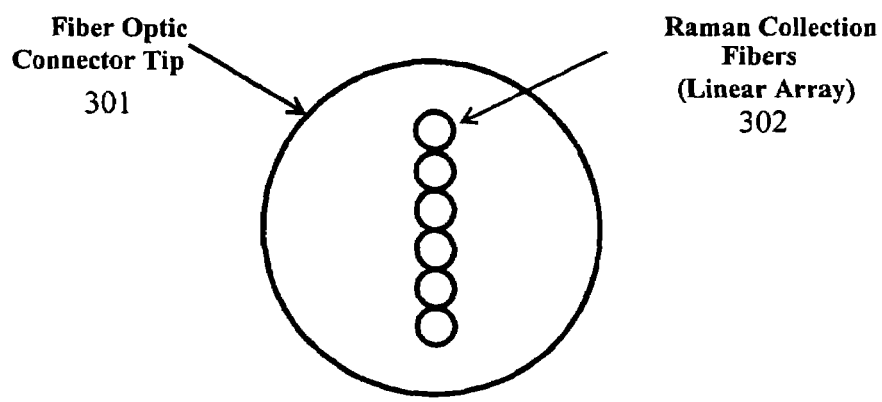
FIG. 3 provides a schematic of an output face of a fiber optic cable, according to an alternate embodiment of the present invention.

The light directed, through the Raman collection fiber tip 301, into the spectrograph from the fiber bundle 302 is arranged in a linear array as shown in FIG. 3 to maximize the optical throughput to the spectrograph by proper alignment with the spectrograph slit-axis. The linear array of 6 fibers is aligned with slit axis of spectrograph to maximize Raman collection signal throughput. Physical dimension of fiber array should not exceed spectrograph slit input height, and core diameters of fibers should match the slit width of the spectrograph. In this case a slit width of 200 μm was used.

Figure 4:
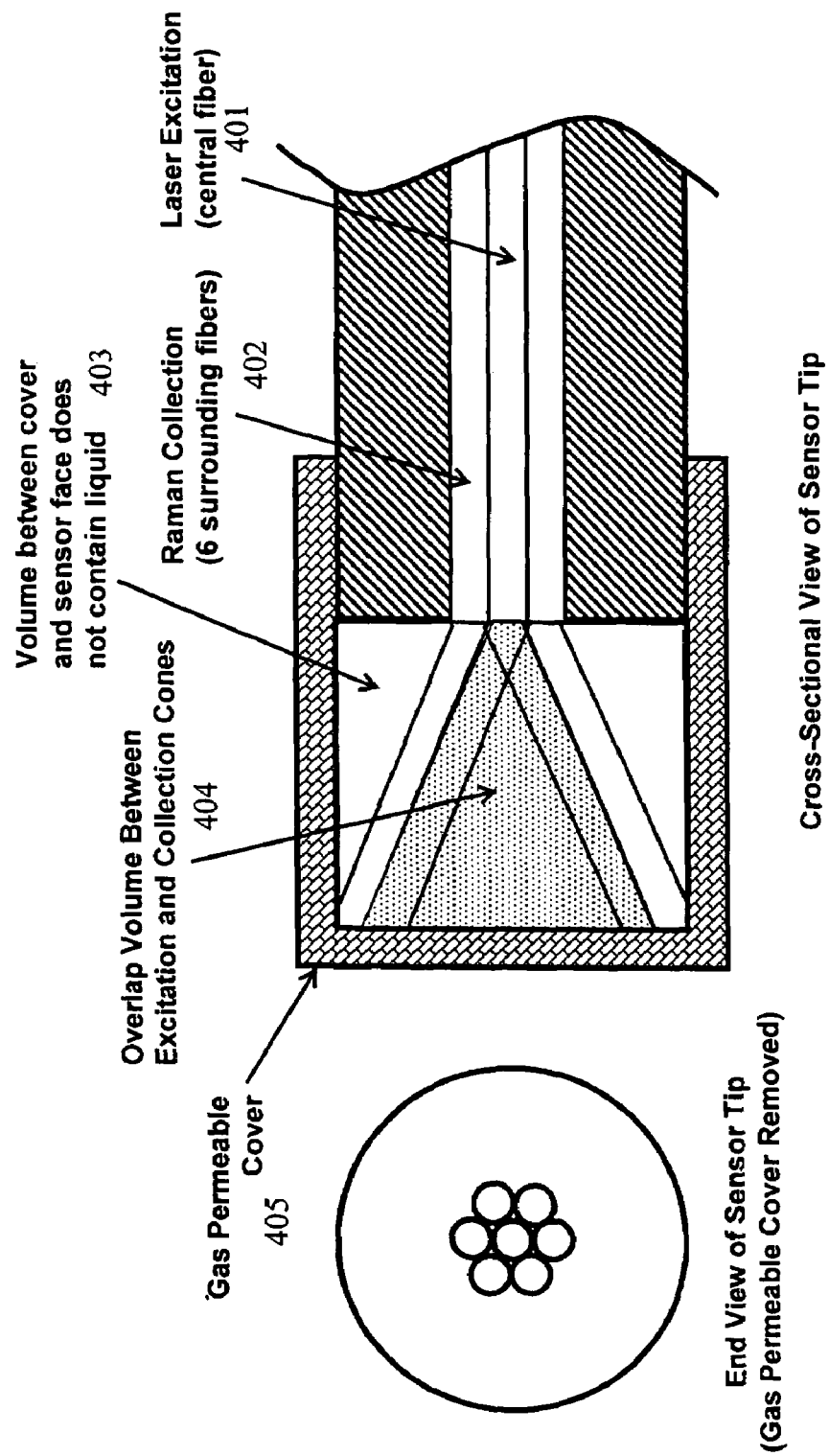
FIG. 4 provides a schematic of an end face of a fiber optic probe tip with permeable gas cover, according to an alternate embodiment of the present invention.

FIG. 4 shows a detail of the fiber optic probe sensor tip which includes a means of preventing liquid fuel from entering and interfering with the gas-phase Raman measurement. Also illustrated are the central laser excitation fiber 401 and the Raman collection fibers 402 surrounding them. The overlap between the excitation and collection cones 404 is also shown. Shown is a porous (gas permeable) cover 405 that is made of a sintered polymer material, a PTFE membrane such as Gore-Tex brand industrial filters, or a graded pore micro-glass fiber filter membrane that is treated with a hydrophobic/oleophobic coating to prevent wetting by hydrocarbon-based liquid fuels, such as those manufactured by Pall Products Co., mounted onto a suitable membrane holder/support structure. Other suitable materials would be highly porous, yet non liquid-permeable solid material with low wettability to prevent liquid fuel saturation, such as a sintered polymer material. The purpose of the gas permeable cover is to prevent liquid fuel droplets from directly contacting the faces of the fiber optic lines, so that there is a volume 403 between the cover and the sensor face that does not contain liquid. This would cause the Raman scattered signal to come from the liquid only and would not represent the gas-phase molecules.

Figure 5:
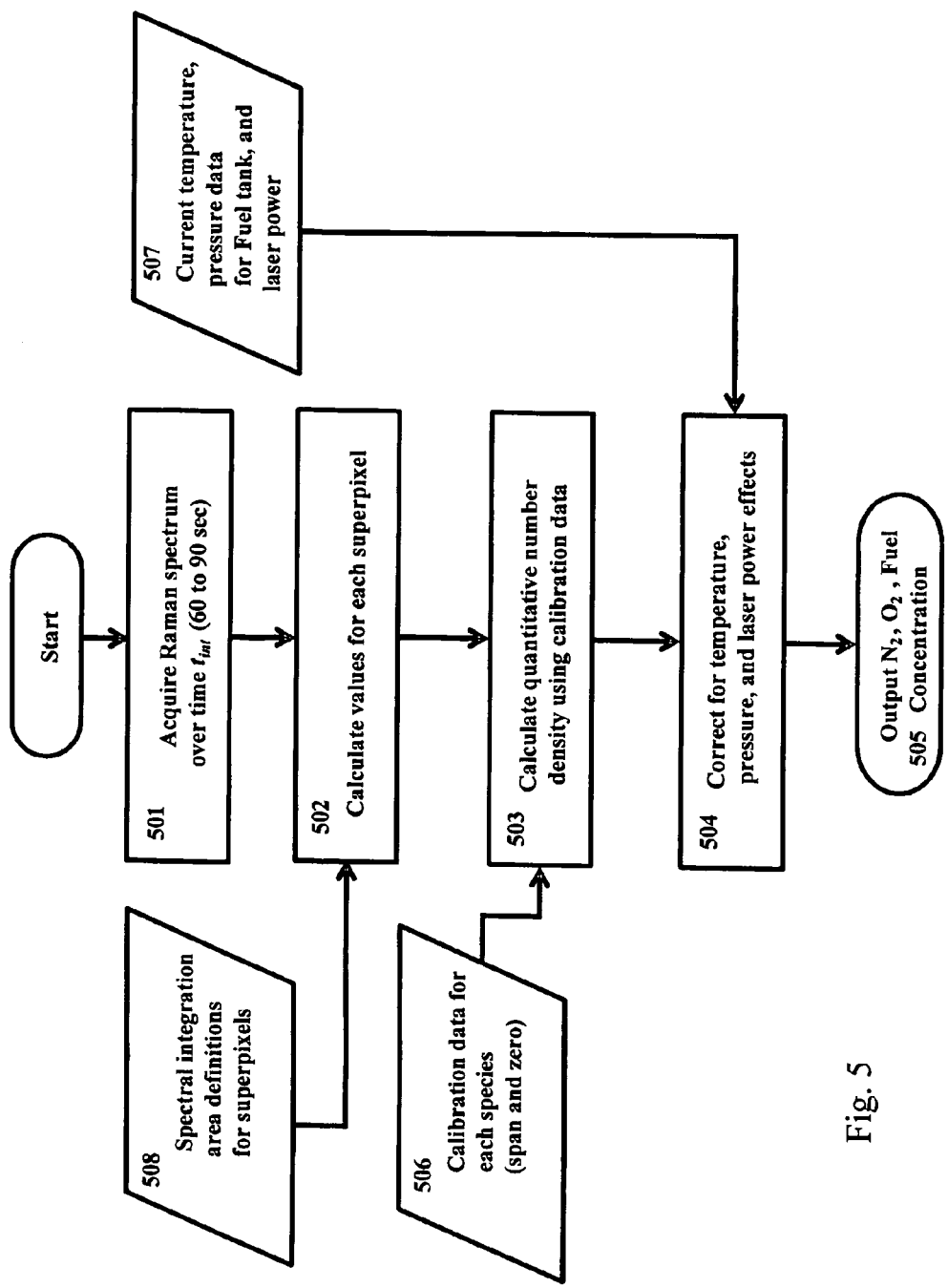
FIG. 5 provides a block diagram of an algorithm used to determine gas concentrations, according to one embodiment of the present invention.

FIG. 5 provides a block diagram of algorithm used for determination of $N_2$, $O_2$, and fuel vapor in Raman scattering ullage sensor system. The Raman signal provided from the CCD array (or other type of detector) is then processed using electronic circuitry or with a computer and software. The basic processing algorithm for an array detector is shown in FIG. 5 and is as follows: (501) start the time integration process and collect the Raman spectrum over time period given by $t_{int}$ (60 to 90 sec); (502) calculate the spectrally integrated signals using the superpixel definition (508); (503) calculate the quantitative number density for each species from the calibration Raman data (506) acquired previously; (504) using the ideal gas law, correct for the ambient pressure and temperature effects using the peripheral instrumentation data from the fuel tank (507); (505) provide a value for the concentration of $N_2$, $O_2$, and fuel vapor to the OBIGGS control system at an interval determined by the integration time set in step (501) which is typically 60 to 90 seconds. Note that a sliding-window integration time may be used in the case of discrete detectors that have a continuous data output (such as PMT's or APD's) representing photon counts. For this type of detection scheme, a continuous sliding-window allows a faster update time than $t_{int}$, by indicating the trend of the change in the signals. However, the full amount of time given by $t_{int}$, must be used to make a determination of the concentration within the required precision.

In operation, the sensor probe is mounted into a fuel tank using a bulkhead feed-through fitting or a flange type mount depending on the physical dimensions of the probe sensor body. The laser and spectrograph/detector can be remotely mounted away from the harsh environment of the fuel tank (such as in the avionics/instrumentation cabinet). The Raman signal collected by the sensor probe is continuously analyzed and accumulated in software or by using a sliding integration window that ranges from about 60 to 90 seconds wide. The value of the concentrations determined by the processor unit utilizing the algorithm described in FIG. 5 is then used to control the rate of inerting gas produced by the OBIGGS, and can also be used to determine the level of safety that exists in the fuel tank being monitored by the sensor system.

Figure 6:
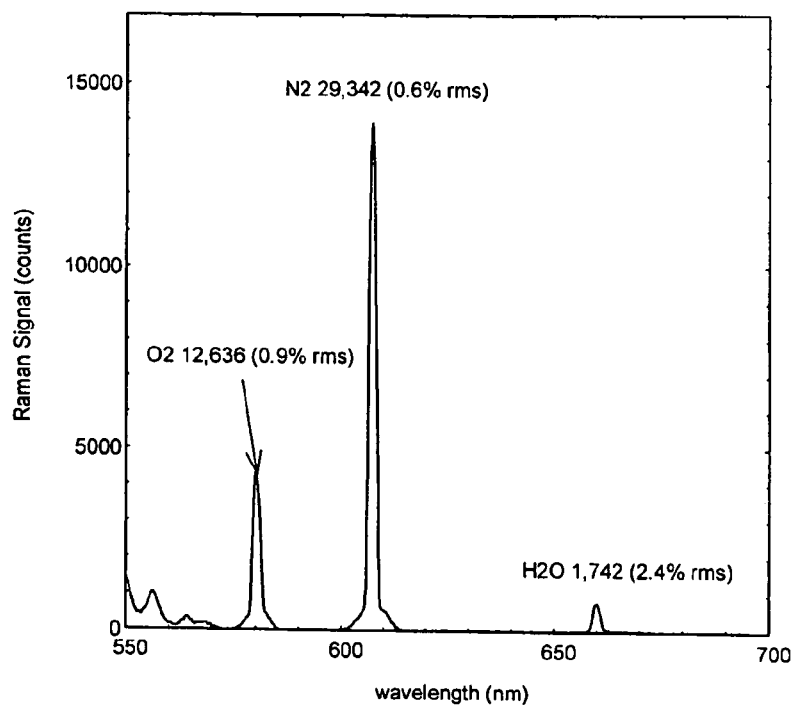
FIG. 6 provides Raman scattering data of ambient air, according to one embodiment of the present invention.

FIG. 6 provides data showing signals from ambient air (26 C) acquired using fiber optic Raman sensor probe. Spectrum was acquired in 90 seconds using 20 mW of 532 nm laser excitation from a DPSS Nd:YVO$_4$ laser. The CCD detector was cooled to –115 C to minimize dark counts. Vibrational band integrated signal values are shown above for each species; signal root-mean-square (rms) values represent one standard deviation (precision) of integrated values assuming Poisson statistics. It is noted that even ambient water vapor was detected. Data was obtained without gas permeable sensor cover.

The system efficiency can be computed based on FIG. 6 for measuring $O_2$ molecules as about 7 photon-counts $mW^{-1}s^{-1}$ for about 21% $O_2$ by volume in air at 1 atm pressure and 26 C. This means that to get 10,000 photon-counts (1% rms) will require about 71 seconds at 20 mW. With a 30 mW laser only about 47 seconds is required. Performing the same analysis for $N_2$, it can be seen from FIG. 10 that 16.3 photon-counts $mW^{-1}s^{-1}$ are determined for about 79% $N_2$ by volume. This means that about 31 seconds of integration time is required to a measurement of $N_2$ with a precision of 1% (rms). It is noted that as the $O_2$ concentration goes down, the $N_2$ concentration will increase resulting in a tradeoff in the precision between the $O_2$ and $N_2$ measurements due to the $N_2$ enrichment. The ability to capture both $O_2$ and $N_2$ data simultaneously is a great advantage to allowing a higher level of certainty in the overall mixing ratio of $O_2/N_2$.

Figure 7:
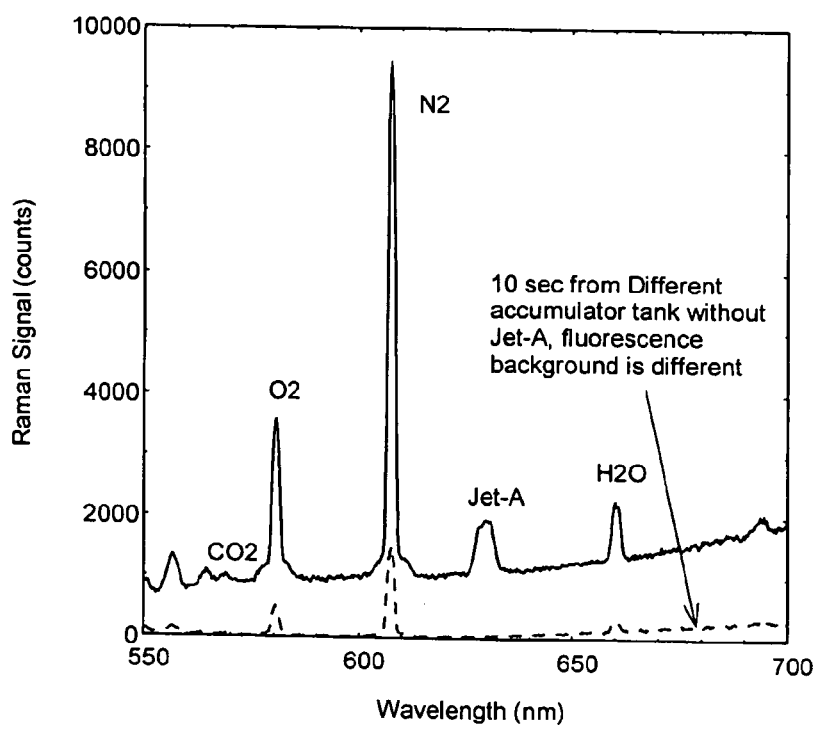
FIG. 7 provides Raman scattering data of jet fuel vapor residue in ambient air, according to one embodiment of the present invention.

FIG. 7, shows data showing signals from jet-A fuel vapor mixed with ambient air (26 C) acquired using fiber optic Raman sensor probe (solid curve) over a 60 second exposure; the dashed curve shows the spectrum for air only with only a 10 second exposure. Spectrum was acquired using 20 mW of 532 nm laser excitation with the CCD detector cooled to –115 C. The vibrational bands for each species are centered at the following wavelengths: 580 nm, 607 nm, and 630 nm, for $O_2$, $N_2$, and jet-A, respectively. By using a 13 nm wide spectral window for each vibrational band, the entire O-Q-S bands can be collected to maximize the signal while minimizing the background noise. The sensitivity of the system enables even ambient water vapor and carbon dioxide to be detected. The data with the jet-A fuel vapor was obtained by placing the probe inside a small cylindrical accumulator vessel to simulate a fuel tank; the fuel tank walls caused some fluorescence background visible as the upward slope. However, by using a zero calibration gas, such as argon or other convenient gas that has zero Raman scattering cross-section, background fluorescence can easily be subtracted as it is a constant. Data shown was obtained without a gas permeable sensor cover.

The performance of the sensor system at a challenging condition representing perhaps the lowest $O_2$ number density that will be encountered by the system in a typical flight envelope: 5% $O_2$ by volume with balance $N_2$ and negligible fuel vapor, –1 C temperature, and 0.2 atm pressure. At this condition, scaling the 7 photon-counts $mW^{-1}s^{-1}$ for a 30 mW laser indicates that about 15.2 minutes of integration time will be required to achieve a 1% precision measurement of $O_2$. Clearly this is too long of a time interval for a 1% precision measurement of $O_2$ concentration. The advantage of the Raman scattering technique is that we simultaneously have a measurement of the inerting gas ($N_2$) which is at much higher concentrations. If we scale the 16.3 photon-counts $mW^{-1}s^{-1}$ for $N_2$ by the 95% concentration of $N_2$ at this condition (by volume) and –1 C and 0.2 atm, we see that it takes only 1.28 minutes for a measurement with 1% precision. With the highly valid assumption that the fuel vapor pressure at –1 C is negligible, thus the balance of the gases simply consists of only $N_2$, we can infer the $O_2$ concentration from the following partial pressure relation: $[O_2]=1-[N_2]$ where the brackets indicate mole fraction. So it is evident that the system is capable of 1% precision measurements of $O_2$ concentration at low pressures within an approximately 1 minute time frame.

Figure 8:
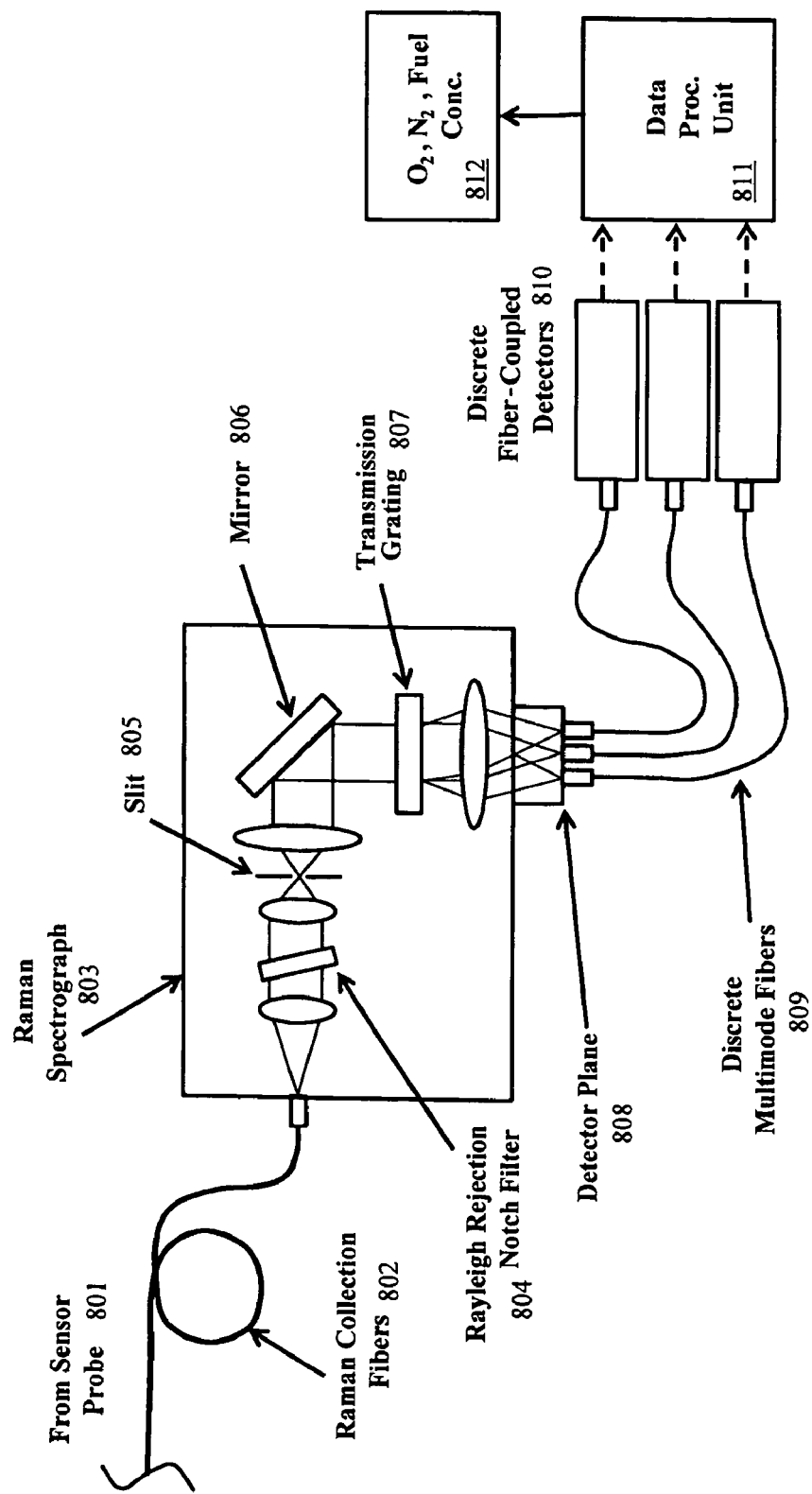
FIG. 8 illustrates a schematic of an alternate embodiment of the system using discrete fiber optically coupled detectors.

FIG. 8 illustrates a schematic of alternate embodiment of system using discrete fiber optically coupled detectors (PMT, APD, etc.) 810 mounted on the exit plane 808 of axially transmissive holographic Raman spectrograph 803 and connected through discrete multimode fibers 809. As in the above-discussed embodiments, the sensor probe 801 introduces light into the spectrograph through the Raman collection fibers 802. The spectrograph utilizes a pre-filter section to reject elastically scattered light (Rayleigh scattering) by use of a spectral notch filter 804 centered at laser wavelength. The spectrograph, as illustrated, also has a slit 805, a mirror 806 and a transmission grating 807. Such filters can be holographic volume phase filters or thin film type filters (rugate) or absorbing colored glass or molecular filters (iodine vapor, etc.). Detectors can be thermo-electrically cooled to reduce dark counts. Data processing unit 811 still needs laser power measurement to normalize Raman signals to provide the gas concentrations 812. The discrete detectors have the potential advantage of lower costs, and of providing a continuous signal stream compared to the CCD array which has to be integrated on-chip, during which time, no signal is produced. The continuous stream signal from discrete detectors can be used in a sliding-window time integration scheme (in hardware or software) to provide a real-time indication of the concentrations in the fuel tank.

Figure 9:
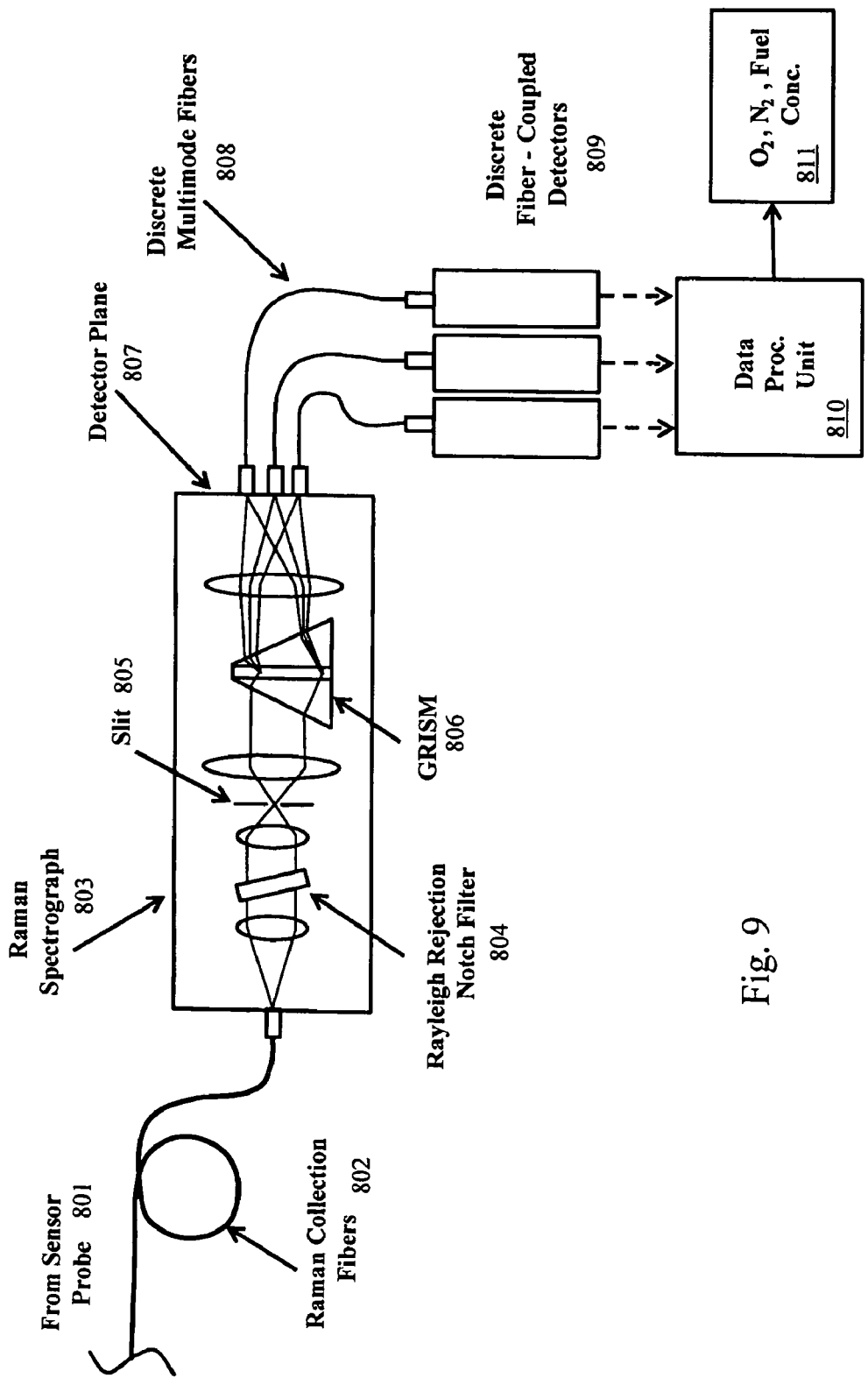
FIG. 9 illustrates a schematic of an alternate embodiment of the system using discrete fiber optically coupled detectors.

FIG. 9 provides a schematic of alternate embodiment of system using discrete fiber optically coupled detectors (PMT, APD, etc.) mounted on the exit plane of axially transmissive holographic Raman spectrograph using grating-prism (GRISM) element 906 to provide dispersion and an undeviated path central wavelength for a compact, high optical throughput spectrograph. The spectrograph with a prism-grating (GRISM) 906 type spectrograph has the advantage of being more compact and easier to align as it provides an undeviated central ray. The GRISM spectrograph also is capable of providing extremely high optical throughput (as fast as f/1.0) if high-speed photographic camera lenses are used. It should be noted that many different spectrograph designs may be used in the present invention. It should also be noted that a CCD array such as depicted in FIG. 1 can be used instead of discrete fiber optic lines at the detector plane in this embodiment.

Figure 10:
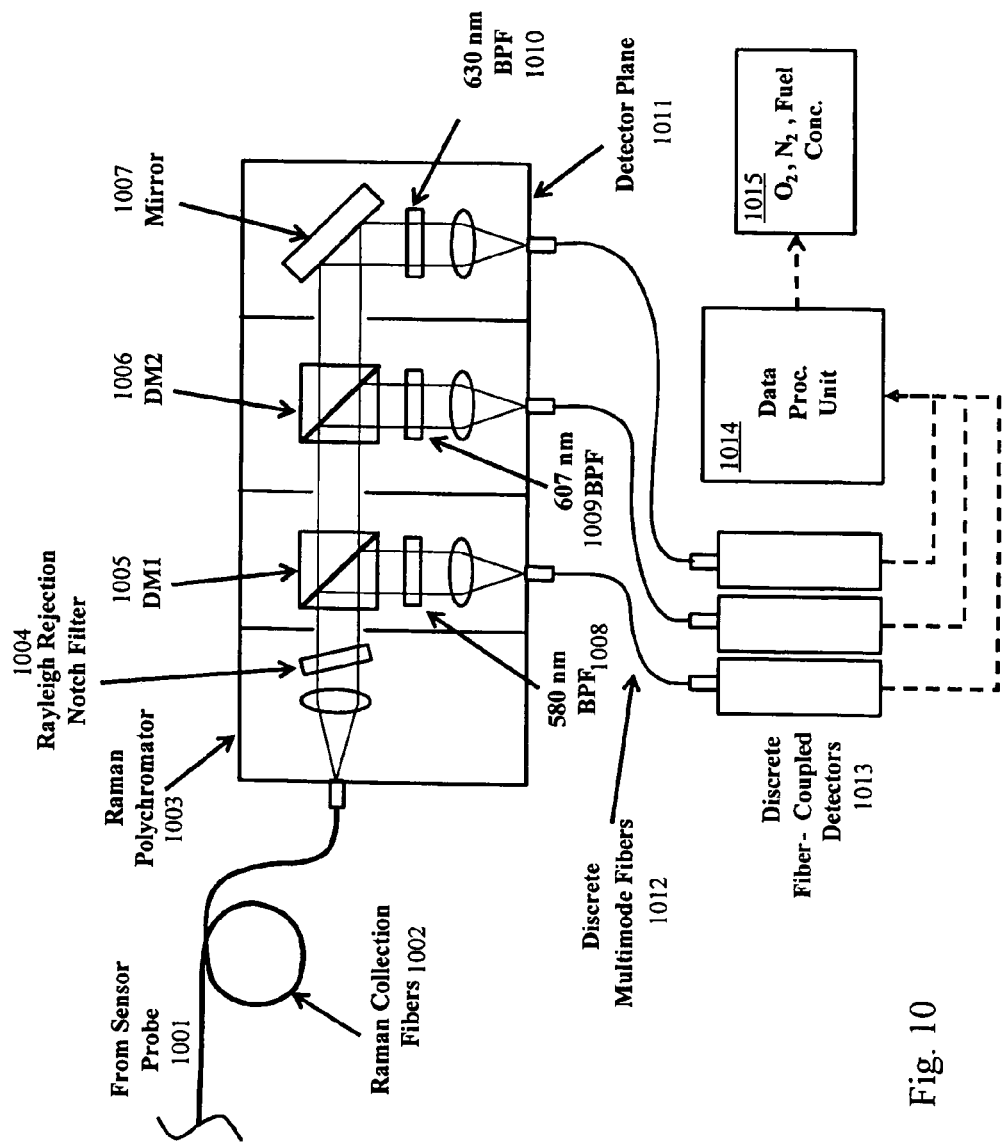
FIG. 10 illustrates a schematic of an alternate embodiment of the system that uses diachronic beam splitters, according to one embodiment of the present invention.

FIG. 10 provides a schematic of an alternate embodiment of system that uses dichroic beam splitters in conjunction with band pass filters to separate the Raman signal into discrete vibrational bands for detection using discrete detectors that are direct coupled or fiber optically coupled (shown). Dichroic beam splitters or mirrors transmit longer wavelengths while reflecting shorter wavelengths. The dichroic mirrors can be thin-film coated type mirrors that transmit a longer wavelength while reflecting a shorter wavelength. Such mirrors are often used for color separation processes. In FIG. 10, in one example, the first dichroic mirror DM1 1005 reflects wavelengths shorter than 590 nm and transmits wavelengths that are longer; the second dichroic mirror DM2 1006 reflects wavelengths shorter than 615 nm and transmits wavelengths that are longer. Band pass filters (BPF) 1008-1010 then provide an approximate 13 nm wide bandwidth centered at 580 nm, 607 nm, and 630 nm, to transmit the Raman signal for $O_2$, $N_2$, and fuel vapor, respectively. In this way, the Raman signal from $O_2$ is directed to the first detector, $N_2$ to the second detector, and fuel vapor to the third detector. The advantages of this type of polychromator include the simplicity of the optical components, its insensitivity to optical misalignment, and a high optical throughput that can approach that of prism or grating based dispersion designs.

Figure 11:
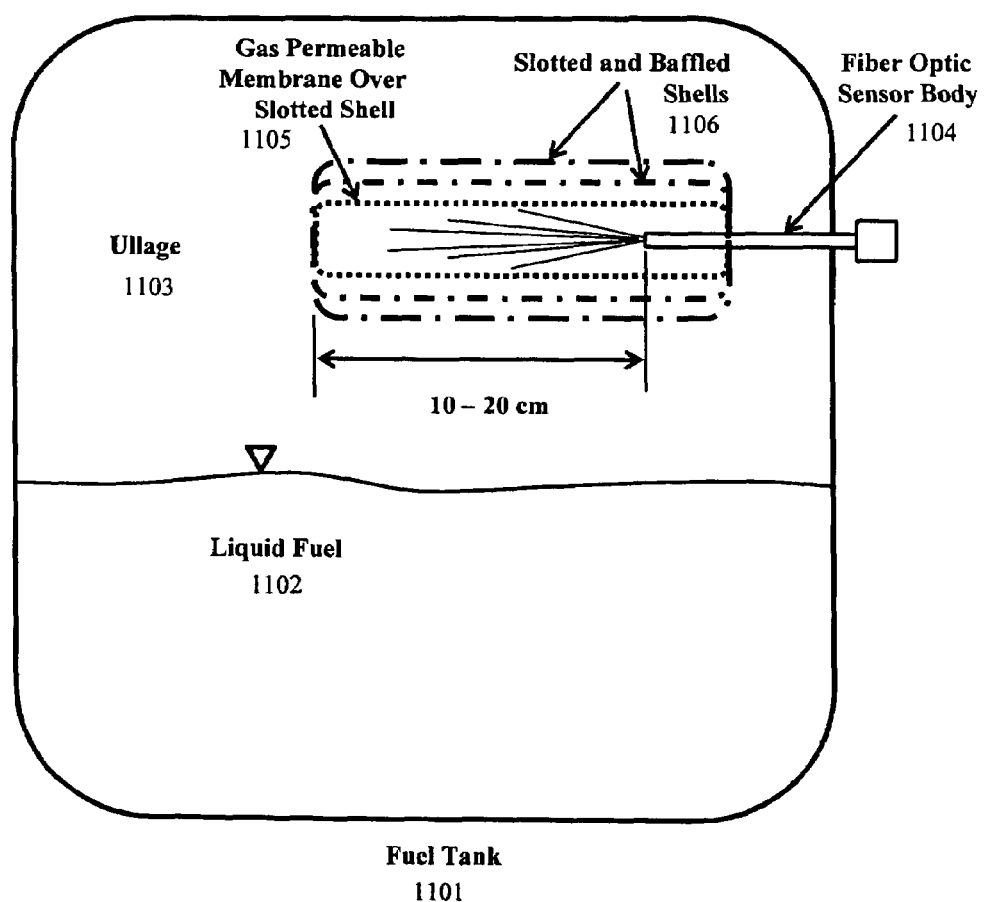
FIG. 11 provides a schematic of a probe sensor head, according to one embodiment of the present invention.
Figure 12:
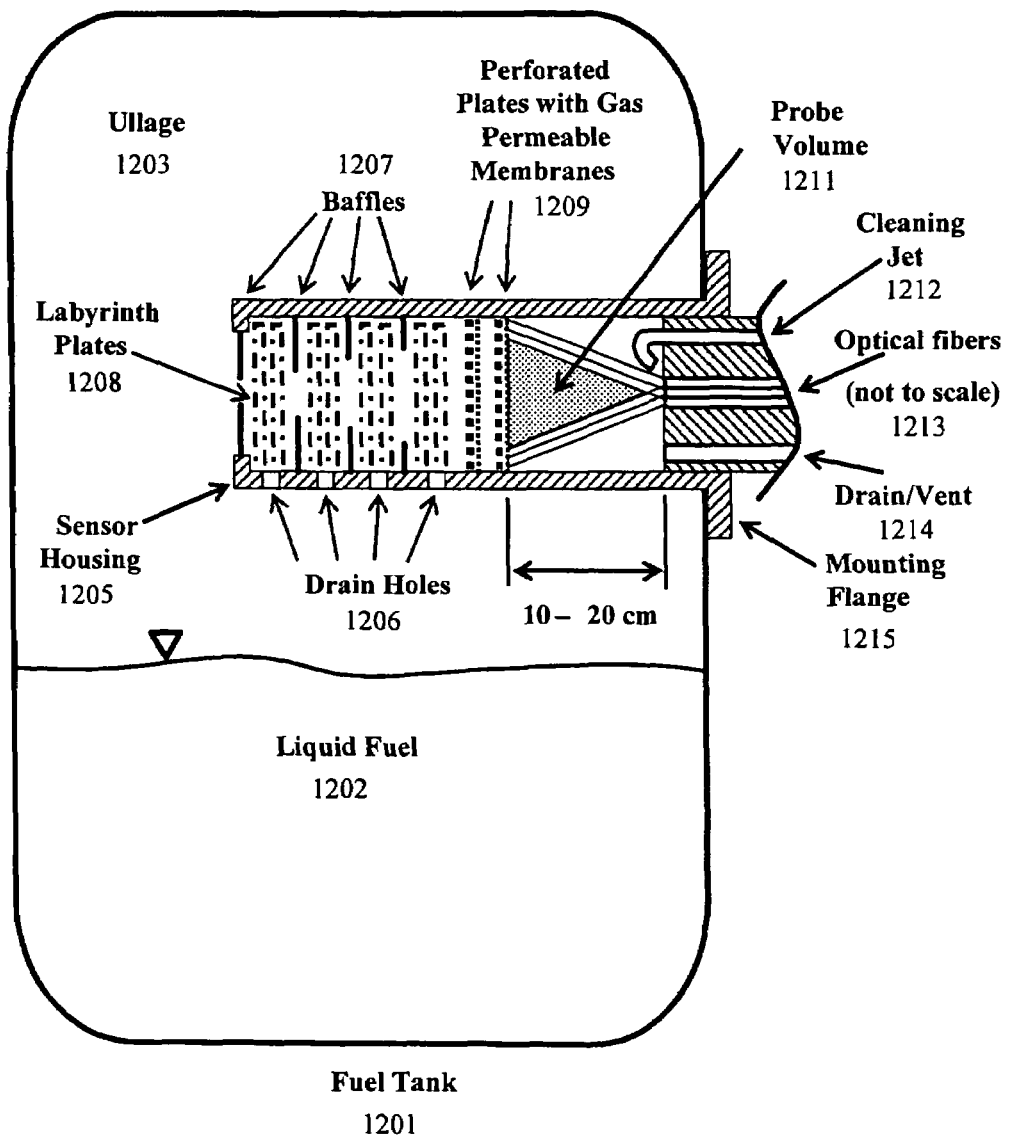
FIG. 12 provides a schematic of a probe sensor head using a cylindrical enclosure with baffle plates, according to one embodiment of the present invention.

FIGS. 11 and 12 illustrate schematics of alternate embodiments of the probe sensor head using a cylindrical enclosure that houses a combination of planar baffle plates with drain holes and labyrinth plates in combination with perforated metal plates that are bonded with gas permeable membranes to prevent liquid entry onto the probe volume. As shown in FIG. 11, the fuel tank 1101 has an amount of liquid fuel 1102 therein, resulting in the ullage 1103. The fiber optic sensor body 1104 is inserted in the fuel tank and is protected by a gas permeable membrane 1105. Slotted and baffled shells 1106 are placed around the membrane to prevent the direct line-of-sight impingement of liquids to the gas permeable membrane mounted behind the successive baffles.

An alternate embodiment is also provided in FIG. 12. The baffles 1207 have a different orientation and are used in conjunction with the labyrinth plates 1208. The labyrinth plates are essentially perforated plates specially designed so that their spacing is conducive to liquid wetting while at the same time, providing ridges and other specially designed surface protrusion that promote the liquid to drip off the labyrinth plates by gravity so that it can exit the drain holes located at the bottom of each baffle plate chamber. The housing 1205 can be mounted to a fuel tank with a flange type seal 1215. Additionally, a small jet 1212 aimed at the fiber faces can be used for the periodic cleaning of the fiber faces with a combination of liquid solvents and clean dry gas flows. A drain/vent tube 1214 (only open when the cleaning jet is used) permits the contaminated cleaning solvent to be removed. Although not shown, each drain hole 1206 itself is baffled to prevent direct liquid entry through the bottom.

The final gas permeable membrane(s) 1209 are bonded to a perforated plate that provides the structural integrity for the membrane. The membrane can be made of a polymer or material with a structure that permits gases to pass through but not liquids (such membranes are commercially available such as Gore-Tex brand industrial filters). The cleaning and vent tubes permit the in-situ periodic calibration of the system by allowing the admission of a zero and span gases. Note that the cleaning and vent tubes are only opened during the cleaning or calibration process, and are normally closed. The valving operation for the cleaning and calibration procedures can be automated using computer controlled solenoid valves located externally to the fuel tank. Another benefit of this embodiment shown in FIG. 12 is that a large volume 1211 beyond the fiber face is provided which does not contribute to a Raman or Rayleigh scattering signature as would be the case from the membrane or porous cover placed in direct vicinity of the probe tip. Since the collection efficiency of the fiber falls off as $1/r^2$, by permitting a sufficient distance of about 10 to 20 cm beyond the fiber face prevents Raman scattering from the gas permeable cover surface to interfere with the gas phase Raman signal.

According to other embodiments of this invention, the fiber optic sensor system simultaneously measures the volumetric concentration of multiple gas-phase species including oxygen, nitrogen, hydrogen, carbon monoxide, carbon dioxide, water vapor, and bulk concentrations of mixed hydrocarbons, such as aliphatics, solvents, kerosene, gasoline, jet fuel, etc. The system provides an accurate and quantitative identification of vapors and gases using a compact spectroscopic means with an accuracy of better than 1%, updating information in near real-time (5 second intervals) at ambient temperature and pressure.

Figure 13:
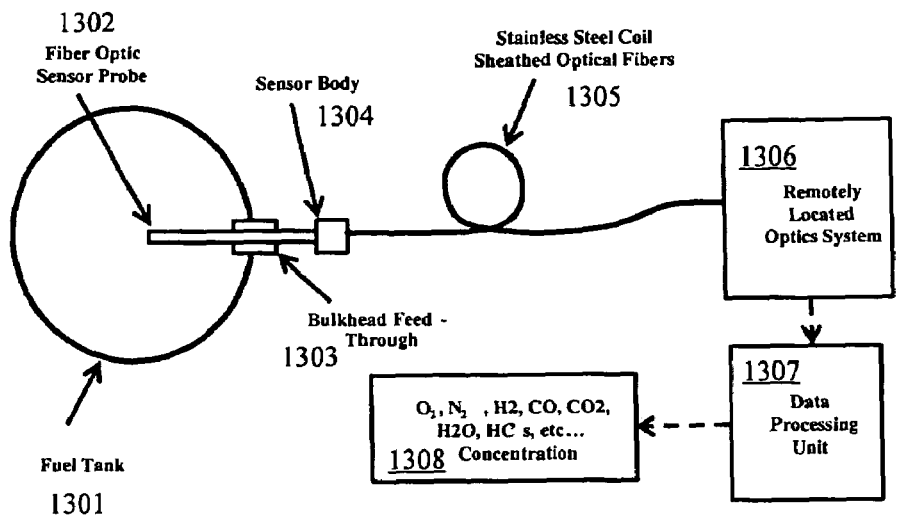
FIG. 13 provides an alternate embodiment of a in-tank ullage flammability sensor, according to one embodiment of the present invention.

The fiber optic sensor probe 1302, as illustrated in FIG. 13, permits remotely located measurements and can be utilized with standard flange, threaded, compression or bulkhead 1303 process fittings for straightforward implementation. Its design is simple and robust with no protruding external components to clog, wear-out, or otherwise go out of alignment. The overall system is rugged, compact for portability, providing long-term reliability and ease of use. Alternatively, the system can be readily integrated with distributive or central control systems 1306 for improved monitoring and control. One application, as discussed above, can be to monitor gases in a fuel chamber 1301. The analysis system 1307 and 1308 can be far away from the tank, as it is connected by stainless steel coiled sheathed optical fibers 1305.

The fiber optic probe 1302 utilizes a low power (<30 mW) diode laser within the measurement zone that is far below ignition energies making the probe intrinsically safe. Additionally, the probe can withstand high temperatures (500 C without cooling) and pressures (>150 bar) encountered in many chemical and industrial process environments. The common wetted material is fused silica (quartz) optical fiber while the casing material may be any metal or polymer material for process compatibility. For applications where the process stream is multiphase or contains liquids, a phase separator such as, a graded pore micro-glass fiber membrane with hydrophobic/oleophobic coating, or a polymer fiber matrix membrane such as Goretex may be utilized to prevent liquids from fouling the probe face.

Examples of applications for this sensor system include: measuring ratios of $O_2$:$N_2$ in on-site generation systems (membrane, PSA VPSA, etc.); measuring $H_2O$ content in dryers or process streams; measuring ratios of $O_2$ to combustible gases such as hydrocarbons or $H_2$ for safety purposes; monitoring the inerting of vessels, tanks and reactor processes; monitoring the ratios of $H_2$:CO in syn-gas processes or fuel reforming processes; and monitoring the headspace in chemical storage tanks or fuel tanks for explosive mixtures, etc.

Figure 14:
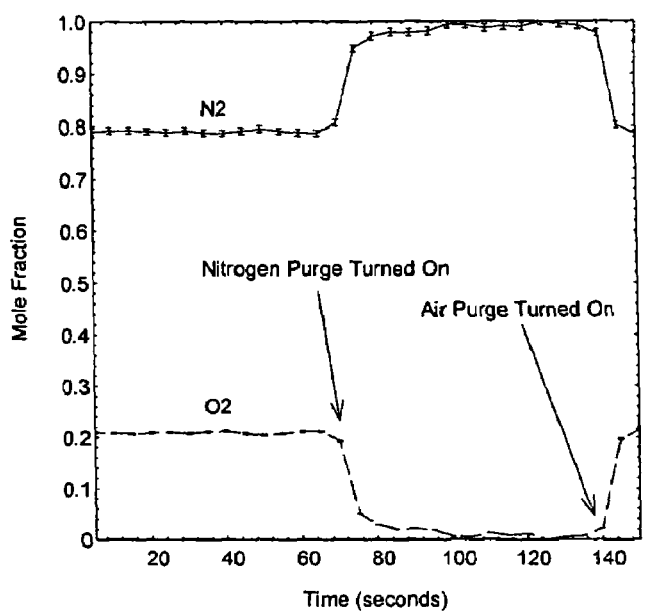
FIG. 14 provides a graph of real-time multi-species gas sensing using a fiber optic probe, according to one embodiment of the present invention.

Since the signals are proportional to molar concentrations, higher total pressure systems provide stronger signals and measurement precision is proportional to the square root of the measurement time. A graph presented in FIG. 14 provides data showing relative compositions of gases, and their associated error bars depicting the measurement precision (calculated from the signal levels using Poisson statistics,) and their real-time changes. Thus, a measurement with 2% precision requires about 1.25 seconds. Similarly, in high pressure systems such as a 30 bar process stream, less than 0.2 seconds is required for a measurement with 1% precision.

Figure 15:
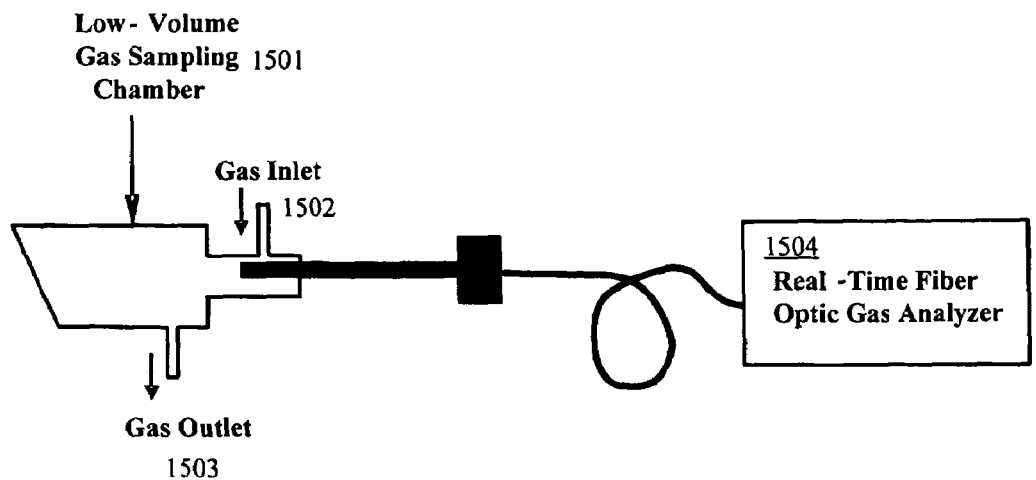
FIG. 15 provides an alternate embodiment of a multi-species chemical gas sensing system, according to one embodiment of the present invention.
Figure 16:
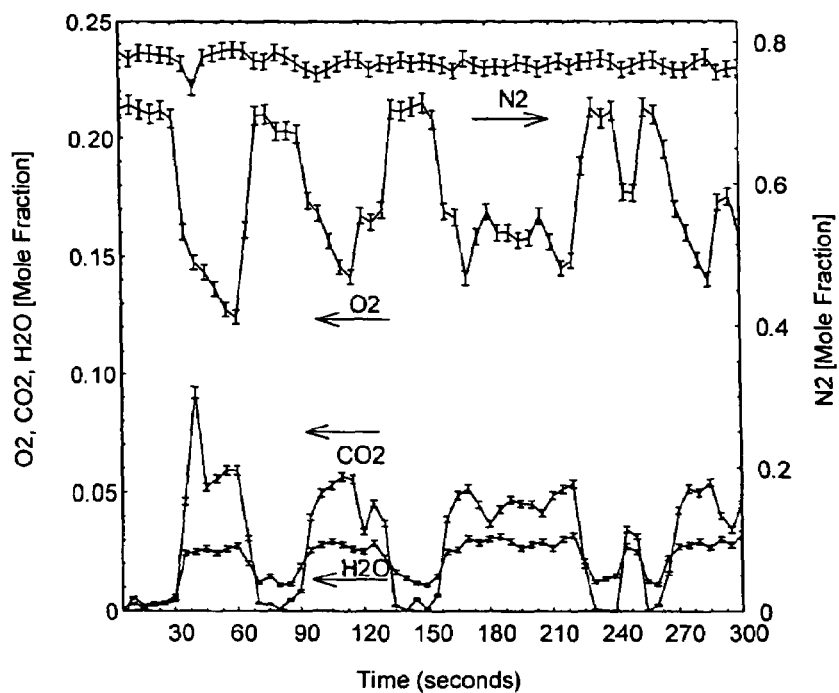
FIG. 16 provides a graph of real-time respiration gas monitoring using a fiber optic probe, according to one embodiment of the present invention.

Additionally, the present invention is also applicable to systems where real-time monitoring of gas species is important. As illustrated in FIG. 15, the real-time fiber optic gas analyzer 1504, is attached to a probe that is inserted into a low-volume gas sampling chamber 1501, having a gas inlet 1502 and a gas outlet 1503. Real-time results of mole fractions of gas species from respiration are presented in FIG. 16. The system has advantages in that it has a five second update interval that allows for feedback control and critical time-dependent process monitoring. Such a system also allows for the monitoring and analysis of a greater number of species and provides a 1% precision rate over five seconds or less.

Figure 17:
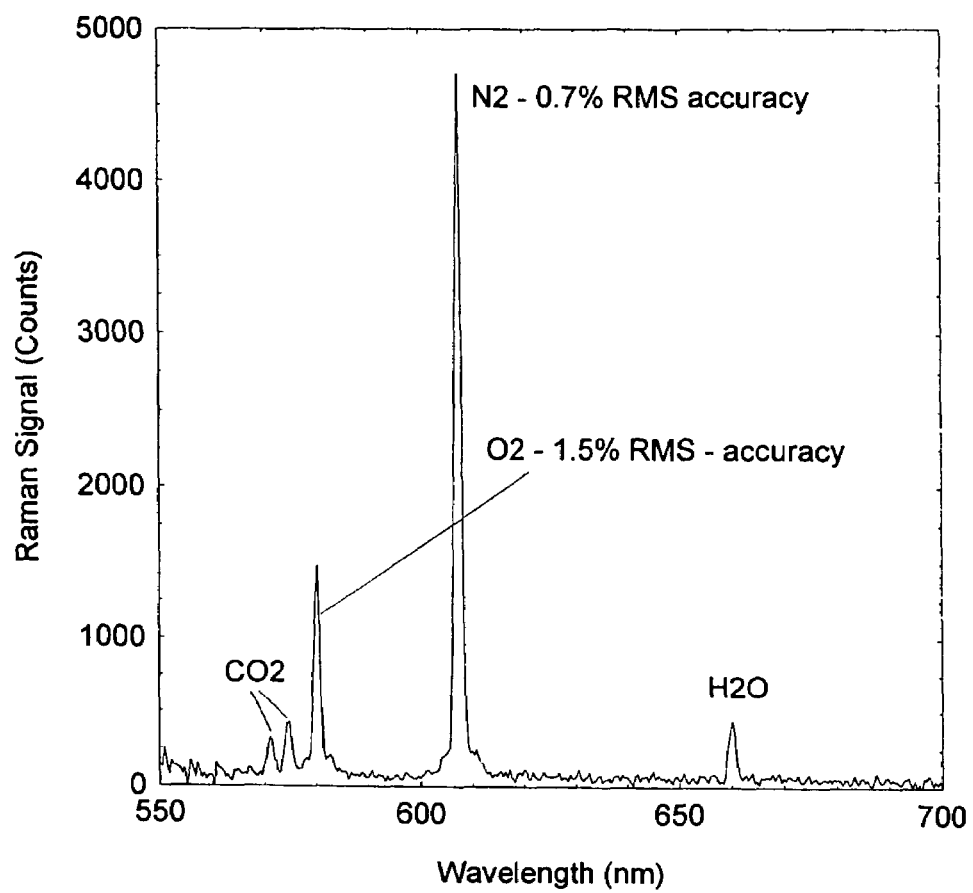
FIG. 17 provides Raman scattering data of gas compositions in human exhaled breath, according to one embodiment of the present invention.
Figure 18:
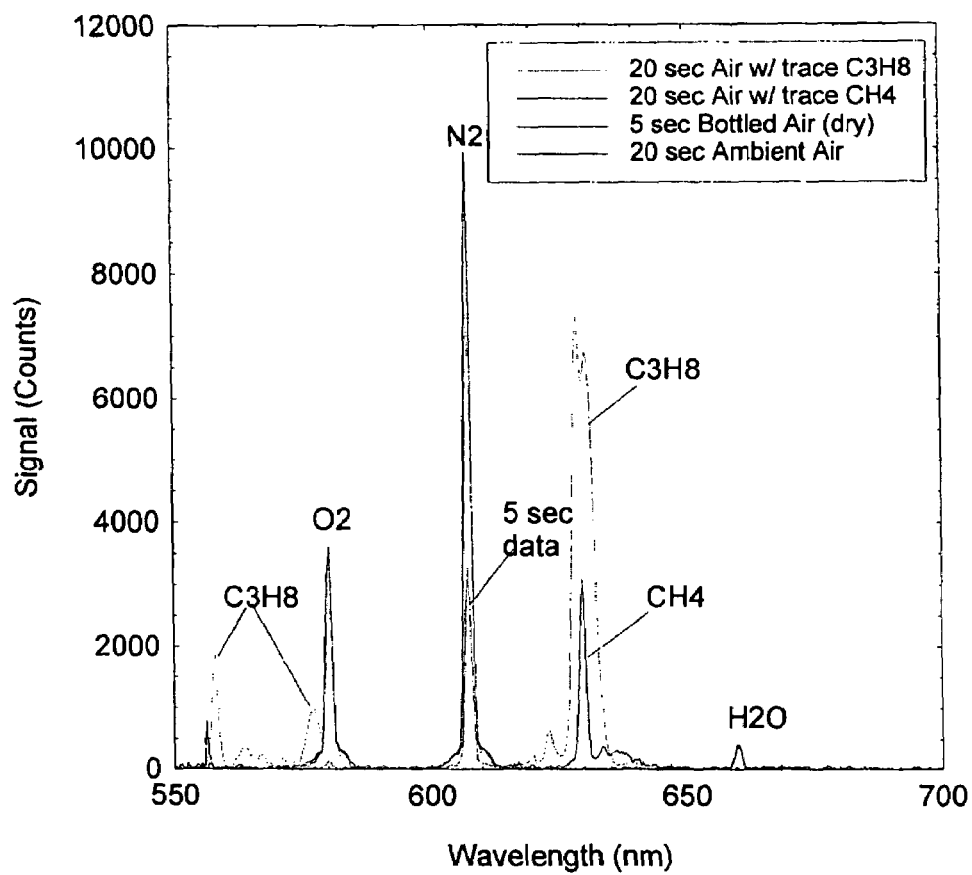
FIG. 18 provides Raman scattering data from measurements for determining ullage flammability, according to one embodiment of the present invention.

In such a system, in this embodiment, can have a different probe design that uses more fibers, but with smaller diameter and higher numerical aperture fibers (0.37 NA). The design uses a single fiber surrounded by 18 fibers in a hexagonal closest packed array similar to the original design. The 18 collection fibers go to an 18×1 linear array that is aligned with the spectrograph slit axis. All 19 fibers are 100 micron core, high OH content, 0.37 NA silica/silica. This permits higher spectral resolution, yet with more light collection. In yet another embodiment, the probe design can have a single fiber surrounded by 97×100 micron core diameter 0.37 NA collection fibers to increase the collection efficiency by a factor of about 5.4× over the 18 fiber version described above. The use of 97×100 micron core fibers with 125 micron diameter cladding results in a linear array height of about 12 mm which completely fills a 12 mm tall detector array, while providing a high degree of spectral resolution provided by a 100 micron slit width. Examples of results using the 18 fiber system are provided in FIGS. 17 and 18, with FIG. 18 providing Raman scattering results for comparing levels of $CH_4$ and $C3H_8$ and in FIG. 17 showing chemical species and concentrations in exhaled human breath. Note that the signal levels would be 5.4× greater with the 97 fiber version, allowing for either an increase the data collection speed, or improved measurement precision.

The theory for Spontaneous Raman scattering is well known. For the purposes of estimating Raman scattering signals for gas density measurements, the vibrational Raman scattering signal S (photon-counts) from a molecular species i over a certain period of time can be simplified to the following engineering relationship:

$$S = E_{LASER} C_{SYS} \Omega_{COLL} V_{PROBE} K_i N_i, \qquad (1)$$

where $E_{LASER}$ is the laser energy in Joules (J), $C_{SYS}$ is an overall system collection constant that represents the optical to photo-electron (photon-count) efficiency per unit scattering cross-section-Joule (photon-counts $cm^{-2}J^{-1}$), $N_{COLL}$ is the collection solid angle in steradians (sr), $V_{PROBE}$ is the volume of the probed molecules ($cm^3$), K is the Raman scattering cross-section per unit molecule·steradian ($cm^2$ $molec^{-1}sr^{-1}$), and N is the number density (molec $cm^{-3}$).

Equation (1) states that the Raman scattering signal is proportional to the laser energy, the molecular species, the volume of the probed molecules, and the number density of the molecular species. This relationship says that if the very weak signals from Raman scattering are to be maximized, the laser energy, the collection efficiency, collection solid angle, and the probed volume must be maximized, with everything else being equal. State of the art gas-phase Raman scattering systems provide about 18,300 photon-counts per Joule of 532 nm light for ambient $N_2$ using an approximate 10 ns long laser pulses (ca. 100 MW power). If a low power (20-30 mW) CW laser is used, over a period of 90 seconds, it delivers 1.8 J of energy. However, a 20-30 mW power level is low enough so that it does not serve as an ignition source, provided that it is not focused to a small spot (the analysis of the ignition potential will be discussed in detail in a later section).

Furthermore, over a period of 90 seconds, the thermal dissipation of the laser light over a large area prevents any significant thermal buildup that can lead to ignition. The collection efficiency and solid angle are further increased by use of multiple fibers arranged around a central illumination fiber, which also serves to increase the collection volume for the signal. Finally, by using highly sensitive backside-illuminated CCD array detector, we can increase the quantum efficiency of the detector. The present CW fiber coupled system can expect approximately 32,000 photon-counts with the 20 mW CW laser system over a 90 second integration span. Since Raman scattering is described by Poisson statistics, the root-mean-square (rms) standard deviation of this signal is simply the square root of 32,000, which is 179, or a 0.56% precision.

This technology permits the in-situ measurement of gaseous $N_2$, $O_2$ and fuel vapor in the ullage of a fuel tank without exposing the tank to any intrinsic explosion or fire safety hazard. The measurement technique is spontaneous laser Raman scattering which enables the simultaneous measurement of multiple chemical species. The simultaneous measurement of all major gas species enables an accurate calculation of the mixing ratio for each species without the assumption of the balance (remaining unmeasured species). The Raman measurement is implemented using fiber optic coupling which is inherently safe since there are no electrical wires that would pose an electrical ignition hazard. The fiber optic coupling also enables the sensor to be remotely located away from the excitation laser and spectrograph. The system requires little electrical power (less than 50 W). The system is compact, robust, and can be made flight hardened as the laser source is solid state. Because the laser and spectrograph/detectors are remotely located (can be in a conveniently accessible place), makes them easy to service or replace in the field. The use of the 532 nm (green) laser wavelength permits the vibrational Raman scattering signals to be measured using low-cost highly efficient visible optics such as silica fibers, highly aberration corrected anti-reflection (AR) coated camera lenses, and Si-based detectors (CCD's and APD's) that are most sensitive to red wavelengths. By using the green 532 nm wavelength, the Raman scattering efficiency is also better than by using red wavelength lasers as the Raman scattering efficiency is inversely proportional to the wavelength to the third power. Using red wavelength lasers also require the detector to be sensitive to near infrared and infrared wavelengths as the vibrational Raman shift for scattering from a 780 nm excitation laser is near 1000 nm. At these wavelengths, the sensitivity of Si-based detectors is reduced and thermal noise counts are more problematic.

There are no inherent electrical discharge ignition sources since system is fiber optically coupled. Raman scattering provides simultaneous multi-species measurement. Fiber coupling permits remote mounting of sensor and convenient mounting of laser and spectrograph. System is compact, rugged and solid state. No consumables to wear out (as compared to electrochemical $O_2$ sensors). System uses little electrical power. The ability to measure $N_2$ concentration in addition to $O_2$ provides an extra measure of reliability since a true $O_2/N_2$ mixing ratio can be made without any assumptions of the balance gas. The mixing ratio can also be used to infer the $O_2$ concentration based on $N_2$ concentration when the $O_2$ density is low (such as when the pressure is low due to altitude). Multiple lasers can be used with multiple excitation fibers for in-flight redundancy. Fiber sensors can be multiplexed so that multiple sensor probes can be monitored using one laser and spectrograph. If an imaging spectrograph and CCD array detector is used, multiple sensor probes can be monitored simultaneously with only one spectrograph/detector (but multiple lasers will still be needed). Thus it is possible to monitor all three or more fuel tanks in an airplane with one spectrograph/CCD array and multiple lasers. This can save system complexity and reduce costs.

The laser and optical systems in general are robust if hard mounted for flight use. The laser system is solid state and is very robust. It has a continuous operational lifetime of about 10,000 hours. Since it is fiber optically coupled, it may be services or replaced in a convenient location without having to access the fuel tank area in an aircraft. Such areas are usually very difficult to access. Furthermore, if multiple excitation fibers are used, then they can be connected to multiple and separate lasers for redundancy. Thus if one laser fails, another can be switched on in-flight without any down time.

It can be confirmed that the fiber optically coupled Raman sensor does not pose an intrinsic ignition hazard. An accepted minimum ignition energy for jet fuel vapor in air resulting from an electrical sparks is approximately 0.25 mJ in a 1 µs duration. This is equal to about 250 W of power over a small spark kernel that is circa 1 mm in diameter or 25 kW $cm^{-2}$. The laser power delivered by the present technology on the other hand is only 30 mW which is about 8000 times less power than spark. Even when the small fiber diameter of 0.20 mm is accounted for, the power density is only 75 W $cm^{-2}$, which is a factor of over 300 less than the value from the spark ignition source. Furthermore, these values are assuming that all the power from the laser is absorbed and converted to heat before it is dissipated. The 532 nm wavelength scatters very well from metal surfaces (such as aluminum fuel tanks) with very little absorption and is optically transparent to jet fuel. Thus the laser power will diverge and be harmlessly dissipated over a broad volume without any significant thermal buildup.

In the case of carbon composite fuel tanks that do absorb the laser radiation, the fuel tank surface just needs to be located several cm away from the fiber optic face to prevent a concentrated light beam from impinging on the fuel tank surface. It is noted that this concern is really not an issue as the gas permeable cover that surrounds and captures the laser emission permits the laser to be absorbed over a broad area with a highly broad-band scattering material that does not absorb 532 nm light readily (white colored PTFE membrane such as Gore-Tex brand membrane filters). Furthermore, the metal shield and baffles surrounding the membrane can serve as a flame arrestor should an ignition source occur within the probe volume, although that is highly unlikely given the results of the above analysis.

The laser source can be any wavelength from 266 nm to 1064 nm, and can be a diode laser such as those with emission at or near 405 nm, 635 nm, 670 nm, 780 nm, 820 nm, etc, or a gas laser such as a HeNe, HeCd, Ar-ion, or other solid-state laser material including Nd:YAG, Nd:YLF, etc. The fiber optic assembly is not limited to 7 fibers but can be any number ranging from 2 to 100, and not limited to 200 µm core diameter but can range from 5 µm to 1000 µm; and does not have to be made of silica but can be sapphire, or fluoride glass, etc. Furthermore, the illumination can be provided by more than one fiber ranging from 2 to 10 and furthermore, the illumination fiber can be single-mode in addition to multi-mode. In addition, the NA of the fiber is not limited to 0.22 but can be lower or higher depending on the fiber material used. However, it is important to match the NA to the f/# of the optics used in the high speed spectrograph. The relationship of $f/\# = (2\,NA)^{-1}$, states that in the case of 0.22 NA, the equivalent f/# is f/2.27. Thus the optics used in the spectrograph should be at least as fast. In the present embodiment f/1.8 optics are well matched to 0.22 NA fibers. In addition, the optical fibers are not limited to solid glass or solid crystal fibers but also include any similar light conduit such as a light pipe or hollow core fiber, or liquid filled light pipes.

The Raman spectrograph mode of operation can be of any type including: reflecting, transmission, etc. The dispersive element can be any type including: gratings (reflection and transmission), prisms, volume phase holographic, grating-prisms (GRISMS), or any combination thereof. The Rayleigh rejection filter can be any type including: colored glass filter, thin-film interference band pass, thin-film rugate type, volume phase holographic interference, molecular absorption filters, etc. or any combination thereof. The high speed spectrograph may also utilize a plurality of dichroic mirrors (or filters) that pass a longer wavelength while reflecting a shorter wavelength, used in combination with a transmission band-pass optical filter to separate the Raman vibrational bands centered at the wavelengths corresponding to oxygen, nitrogen, and fuel vapor at 580 nm, 608 nm, and 630 nm, respectively. Such systems do not require the use of a dispersive optical element such as a grating or prism.

The detector can be an array or discrete and can be any type of sensitive photoelectric device by which a photon is converted into an electrical signal. Such devices include photomultiplier tubes (PMT), avalanche photodiodes (APD), photodiodes, photovoltaic cells, CMOS detector arrays, microchannel detectors, image intensifier detectors, etc. In the case of discrete fibers or detectors though, the input aperture of the fiber or detector is adjusted such that its width satisfies the spectral bandwidth requirement of an approximately 13 nm spectral band pass for each Raman vibrational band that is collected.

The gas permeable cover can be a single piece unit or a multi-piece assembly and may contain multiple gas permeable membranes or porous solid materials or structures, with the common goal of preventing liquid entry into the area immediately surrounding the fiber faces of the probe tip. Additionally, baffles, tortuous passages, labyrinth seals, porous solid structures such as reticulated open-cell metal foams, plastic foams, ceramic foams, etc., can be used in combination with gas permeable membranes to further enhance the liquid separation function. The gas permeable membranes can be made from graded pore micro-glass fiber filter membranes with a hydrophobic/oleophobic surface treatment, or a polymer matrix membrane such as Goretex, or the like.

The measurement probe volume, although assumed to be the ullage of the fuel tank may also include any flow passages, piping or channeling that is connected to the ullage of the fuel tank. This includes the vent line or fill line connected to the ullage or a small chamber or vestibule connected to the ullage. In the case of OBIGSS nitrogen enriched flows from a separation unit, the fiber optic sensor probe head may be located within the pipe or tubing that is used to fill the ullage so that a determination of the $O_2$ concentration in the OBIGGS fill stream may be made.

Although the invention has been described based upon these preferred embodiments, it would be apparent to those skilled in the art that certain modifications, variations, and alternative constructions would be apparent, while remaining within the spirit and scope of the invention. In order to determine the metes and bounds of the invention, therefore, reference should be made to the appended claims.

The invention claimed is:

1. A system for determining gas compositions comprising:
   a probe, inserted into a source of gaseous material, the probe having a gas permeable sensor tip and being capable of sending and receiving light to and from the gaseous material;
   a sensor body, connected to the probe, situated outside of the source;
   a fiber bundle, connected to the sensor body and communicating light to and from the probe;
   a laser source, connected to one portion of the fiber bundle and providing laser light to the fiber bundle and the probe;
   a Raman spectrograph, connected to another portion of the fiber bundle, receiving light from the probe and filtering the received light into specific channels; and
   a data processing unit, receiving and analyzing the received light in the specific channels and outputting concentration of specific gas species in the gaseous material based on the analyzed received light.

2. The system as recited in claim 1, wherein the gaseous material source is a fuel tank and the system is configured to determine the concentration of the specific gas species in a ullage of the fuel tank.

3. The system as recited in claim 1, wherein the gaseous material source is a natural gas pipeline and the system is configured to determine the concentration of the specific gas species in the natural gas pipeline.

4. The system as recited in claim 1, wherein the gaseous material source is a gas sampling chamber receiving gases exhaled from a medical patient and the system is configured to determine the concentration of the specific gas species in the exhaled gases.

5. The system as recited in claim 1, wherein the gaseous material source is a gas sampling chamber receiving anesthesiological gases provided to a medical patient and the system is configured to determine the concentration of the specific gas species in the anesthesiological gases.

6. The system as recited in claim 1, wherein the probe receives optical fibers from the fiber bundle such that optical fibers for laser excitation of the gaseous material are surrounded by other optical fibers for Raman light collection.

7. The system as recited in claim 1, wherein Raman spectrograph comprises discrete optical detectors, with each discrete optical detector detecting filtered light from one channel of the specific channels.

8. The system as recited in claim 1, wherein Raman spectrograph comprises a prism-grating type spectrograph.

9. The system as recited in claim 1, wherein Raman spectrograph comprises dichroic mirrors and spectral band pass filters to filter the received light into the specific channels.

10. The system as recited in claim 1, wherein the probe further comprises a cleaning jet, receiving cleaning fluid and used to clean a light receiving surface of the probe.

11. The system as recited in claim 10, wherein the probe further comprises a drain and vent hole that allows for the cleaning fluid and other liquids to be wicked away.

12. The system as recited in claim 1, wherein the gas permeable sensor tip further comprises a series of baffles and labyrinth plates to limit impingement of liquids to a gas permeable membrane.

13. The system as recited in claim 12, wherein the membrane is composed of a graded pore micro-glass fiber filter with a hydrophobic/oleophobic coating.

14. A method for determining gas compositions of a gaseous material, comprising the steps of:
   receiving laser light, from a laser source, by a probe inserted into a source of gaseous material, the probe having a gas permeable sensor tip;
   receiving Raman light resulting from the laser light excitation of the gaseous material;
   communicating the Raman light to a Raman spectrograph via a fiber bundle;
   filtering the received Raman light into specific channels;
   receiving and analyzing the light in the specific channels by a data processing unit; and
   outputting concentrations of specific gas species in the gaseous material based on the analyzed received light.

15. The method as recited in claim 14, wherein the gaseous material source is a fuel tank and the method determines the concentration of the specific gas species in a ullage of the fuel tank.

16. The method as recited in claim 14, wherein the gaseous material source is a natural gas pipeline and the method determines the concentration of the specific gas species in the natural gas pipeline.

17. The method as recited in claim 14, wherein the gaseous material source is a gas sampling chamber receiving gases exhaled from a medical patient and the method determines the concentration of the specific gas species in the exhaled gases.

18. The method as recited in claim 14, wherein the gaseous material source is a gas sampling chamber receiving anesthesiological gases provided to a medical patient and the method determines the concentration of the specific gas species in the anesthesiological gases.

19. The method as recited in claim 14, wherein the step of filtering the received Raman light comprises filtering the received Raman light through discrete optical detectors, with each discrete optical detector detecting filtered light from one channel of the specific channels.

20. The method as recited in claim 14, wherein the step of filtering the received Raman light comprises filtering the received Raman light through a prism-grating type spectrograph.

21. The method as recited in claim 14, wherein the step of filtering the received Raman light comprises filtering the received Raman light through dichroic mirrors and spectral band pass filters to filter the received light into the specific channels.

22. A system for determining gas compositions of a gaseous material, comprising:
- laser receiving means for receiving laser light, from a laser source, by a probe inserted into a source of gaseous material, the probe having a gas permeable sensor tip;
- Raman receiving means for receiving Raman light resulting from the laser light excitation of the gaseous material;
- communicating means for communicating the Raman light to a Raman spectrograph via a fiber bundle;
- spectrographic means for filtering the received Raman light into specific channels;
- analyzing means for receiving and analyzing the light in the specific channels by a data processing unit; and
- outputting means for outputting concentrations of specific gas species in the gaseous material based on the analyzed received light.

23. The system as recited in claim 22, wherein the gaseous material source is a fuel tank and the system is configured to determine the concentration of the specific gas species in a ullage of the fuel tank.

24. The system as recited in claim 22, wherein the gaseous material source is a natural gas pipeline and the system is configured to determine the concentration of the specific gas species in the natural gas pipeline.

25. The system as recited in claim 22, wherein the gaseous material source is a gas sampling chamber receiving gases exhaled from a medical patient and the system is configured to determine the concentration of the specific gas species in the exhaled gases.

26. The system as recited in claim 22, wherein the gaseous material source is a gas sampling chamber receiving anesthesiological gases provided to a medical patient and the system is configured to determine the concentration of the specific gas species in the anesthesiological gases.

* * * * *

UNITED STATES PATENT AND TRADEMARK OFFICE
CERTIFICATE OF CORRECTION

| | |
|---|---|
| PATENT NO. | : 7,385,692 B1 |
| APPLICATION NO. | : 11/412924 |
| DATED | : June 10, 2008 |
| INVENTOR(S) | : Quang-Viet Nguyen |

It is certified that error appears in the above-identified patent and that said Letters Patent is hereby corrected as shown below:

Section (73) of the Title Page of the Patent should read as follows:

-- Section (73) Assignee: The United States of America as represented by the Administrator of NASA, Washington, DC (US) --

Signed and Sealed this

Sixteenth Day of September, 2008

JON W. DUDAS
*Director of the United States Patent and Trademark Office*